(12) United States Patent
Voegele et al.

(10) Patent No.: US 8,641,608 B2
(45) Date of Patent: Feb. 4, 2014

(54) MANIFOLD FOR LAPAROSCOPIC SEAL ASSEMBLY

(75) Inventors: James W. Voegele, Cincinnati, OH (US); Christopher J. Hess, Cincinnati, OH (US); William B. Weisenburgh, II, Maineville, OH (US); Robert P. Gill, Mason, OH (US); Daniel W. Drew, Loveland, OH (US); Frank L. Lyman, Point Pleasant, NJ (US); Michael D. Cronin, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1228 days.

(21) Appl. No.: 11/979,638

(22) Filed: Nov. 6, 2007

(65) Prior Publication Data
US 2009/0118587 A1    May 7, 2009
US 2011/0306842 A9    Dec. 15, 2011

Related U.S. Application Data

(63) Continuation-in-part of application No. 11/399,045, filed on Apr. 5, 2006, now abandoned.

(60) Provisional application No. 60/669,514, filed on Apr. 8, 2005, provisional application No. 60/700,176, filed on Jul. 18, 2005.

(51) Int. Cl.
    *A61B 1/32*    (2006.01)

(52) U.S. Cl.
    USPC .......................................................... 600/201

(58) Field of Classification Search
    USPC ......... 600/204–208, 212, 213, 585, 245, 248, 600/223; 128/849, 850, 897, 888; 606/42, 606/60
    See application file for complete search history.

(56) References Cited

U.S. PATENT DOCUMENTS

| | | | |
|---|---|---|---|
| 5,437,683 A | 8/1995 | Neumann et al. | |
| 5,522,791 A | 6/1996 | Leyva | |
| 6,033,426 A | 3/2000 | Kaji | |
| 6,165,184 A * | 12/2000 | Verdura et al. | 606/148 |
| 6,811,546 B1 * | 11/2004 | Callas et al. | 604/167.06 |
| 2004/0154624 A1* | 8/2004 | Bonadio et al. | 128/849 |
| 2006/0161049 A1* | 7/2006 | Beane et al. | 600/207 |
| 2006/0247516 A1* | 11/2006 | Hess et al. | 600/426 |
| 2008/0300488 A1* | 12/2008 | Schutz et al. | 600/459 |

* cited by examiner

Primary Examiner — Sameh Boles
(74) Attorney, Agent, or Firm — Welsh Flaxman & Gitler LLC

(57) ABSTRACT

A laparoscopic seal assembly includes a seal cap having a seal with an access opening. The seal cap also includes a manifold connection for attachment of a functional apparatus. The seal assembly further includes a retractor. The functional apparatus may be a finger mounted tether or an insufflations passageway. The functional apparatus may be combined or provided separately.

17 Claims, 13 Drawing Sheets

MANIFOLD FOR LAPAROSCOPIC SEAL ASSEMBLY

CROSS REFERENCE TO RELATED APPLICATIONS

This application is a continuation-in-part of U.S. patent application Ser. No. 11/399,045, entitled "TISSUE MARKER AND METHOD FOR USE", filed Apr. 5, 2006, now abandoned, which claims the benefit of U.S. Provisional Patent Application Ser. Nos. 60/669,514, filed Apr. 8, 2005, and 60/700,176, filed Jul. 18, 2005.

BACKGROUND OF THE INVENTION

1. Field of the Invention

The present invention relates to devices for laparoscopic surgical procedures. More particularly, the invention relates to devices enhancing hand assisted laparoscopic procedures performed in conjunction with a laparoscopic seal assembly.

2. Description of the Related Art

In a minimally invasive, laparoscopic surgical procedure, a surgeon may place a number of small ports into the abdomen to gain access into the abdominal cavity of the patient. A surgeon may use, for example, a port for insufflating the abdominal cavity to create space, a port for introducing a laparoscope for viewing, and a number of other ports for introducing surgical instruments for operating on tissue. The benefits of minimally invasive procedures compared to open surgery procedures for treating certain types of wounds and diseases are now well known to include faster recovery time and less pain for the patient, better outcomes and lower overall costs.

In traditional, open surgery, surgeons may use their hands, together with the surgical instruments to manipulate tissues, to perform particular steps of the procedure and to obtain tactile feedback through their fingertips to verify the nature of particular tissues. Also in open surgery, the size and shape of the instrument that a surgeon may place into the abdominal cavity, as well as the size and shape of tissues that a surgeon may remove, obviously is not nearly as limited as in laparoscopic surgery.

Hand assisted, laparoscopic surgery (HALS) combines some of the benefits of both the open and the laparoscopic methods. In a hand assisted laparoscopic surgical procedure, a surgeon still places small ports into the abdomen to insufflate, to view and to introduce instruments into the abdominal cavity. Additionally, in a HALS procedure, a surgeon also creates an incision into the abdominal wall large enough to accommodate the surgeon's hand. The incision may be retracted and draped to provide a suitably sized and protected opening. A surgeon may also place a laparoscopic access device, also referred to as a laparoscopic seal assembly (or hand access seal assembly, hand access device, HALS seal assembly or HALS access device), into the incision to maintain insufflation in the abdominal cavity while the surgeon's hand is either inserted into the cavity through the laparoscopic seal assembly or removed from the cavity. The advent of HALS and the laparoscopic seal assembly creates numerous opportunities for creating and improving surgical devices and methods.

SUMMARY OF THE INVENTION

It is, therefore, an object of the present invention to provide a laparoscopic seal assembly including a seal cap having a seal with an access opening. The seal cap also includes a manifold connection for attachment of a functional apparatus. The seal assembly further includes a retractor.

It is also an object of the present invention to provide a seal assembly wherein the seal is an iris seal.

It is also another object of the present invention to provide a seal assembly wherein the seal cap includes a housing in which the seal is positioned, and the housing includes an upper seal ring and a lower seal ring coupled together with the seal positioned therebetween for relative movement in a manner opening and closing the seal in a controlled manner.

It is still a further object of the present invention to provide a seal assembly wherein the functional apparatus is a finger-mounted tether.

It is also an object of the present invention to provide a seal assembly wherein the finger-mounted tether includes an accessory attachment recess for selective attachment of various functional components.

It is yet a further object of the present invention to provide a seal assembly wherein the finger-mounted tether includes an energy source.

It is also an object of the present invention to provide a seal assembly wherein the finger-mounted tether includes a fluid port.

It is also another object of the present invention to provide a seal assembly wherein the finger-mounted tether includes a finger-attachment mechanism.

It is also a further object of the present invention to provide a seal assembly wherein the finger-attachment mechanism includes an elastomeric ring shaped and dimensioned to frictionally engage a finger.

It is still another object of the present invention to provide a seal assembly wherein the functional apparatus is an insufflation passageway.

It is also an object of the present invention to provide a seal assembly wherein the insufflation apparatus includes an input port located on an external side of the seal cap, and external tubing links the input port to a gas source.

It is a further object of the present invention to provide a seal assembly wherein the insufflation apparatus further includes a lumen formed with the seal cap and retractor.

It is also an object of the present invention to provide a seal assembly wherein the lumen includes an exit port oriented to supply gas to the abdominal cavity in a manner creating a circular pattern following the natural shape of the seal cap.

It is another object of the present invention to provide a seal assembly wherein the input port includes a stopcock valve.

It is also an object of the present invention to provide a seal assembly wherein the retractor includes a lower retractor ring including a light ring.

It is also a further object of the present invention to provide a seal assembly wherein the light ring is a fiber optic cable.

Other objects and advantages of the present invention will become apparent from the following detailed description when viewed in conjunction with the accompanying drawings, which set forth certain embodiments of the invention.

DESCRIPTION OF THE PREFERRED EMBODIMENTS

Figure 1:
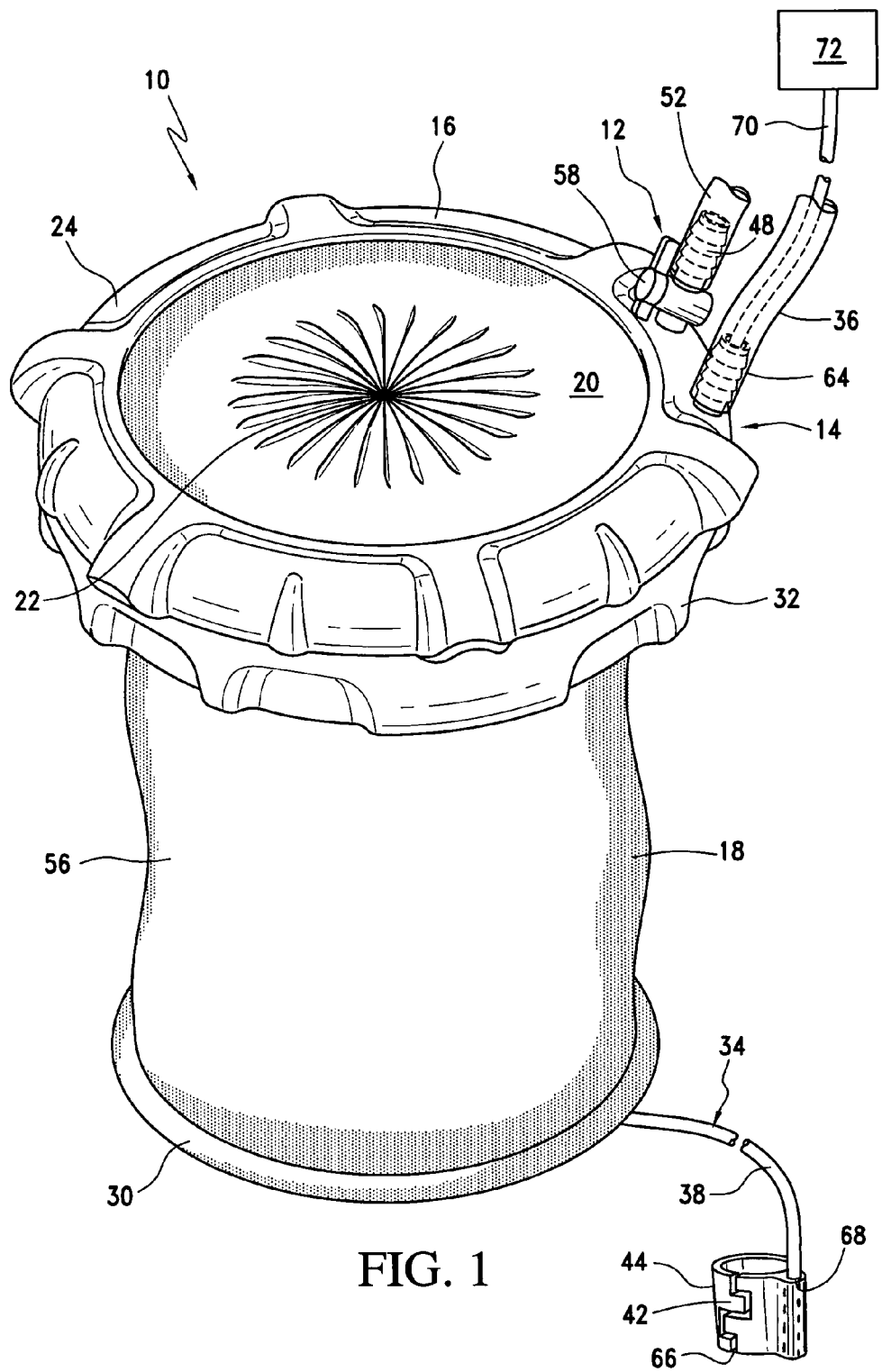
FIG. 1 is a perspective view of a laparoscopic seal assembly in accordance with a preferred embodiment.
Figure 2:
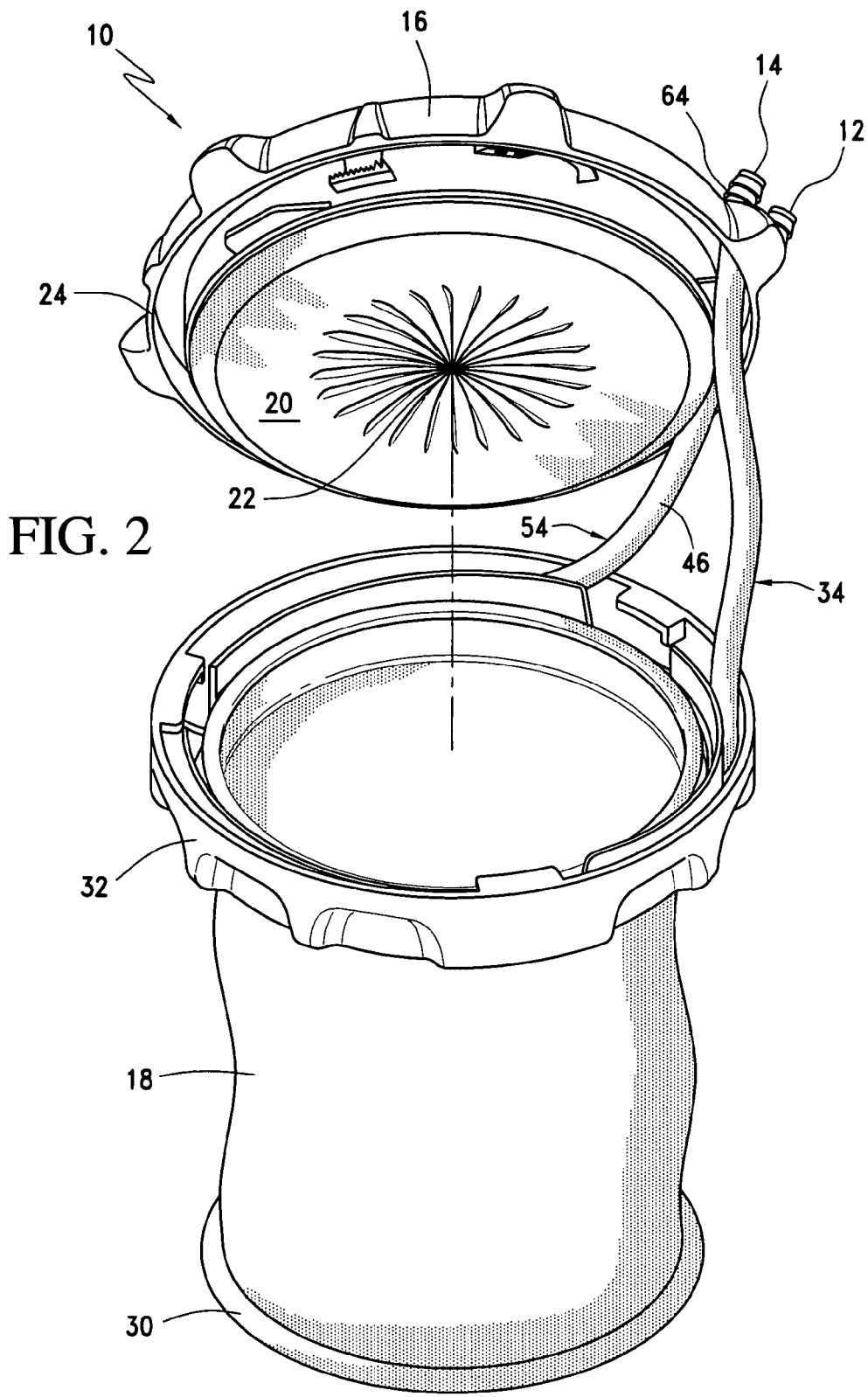
FIG. 2 is a perspective view of the laparoscopic seal assembly shown in FIG. 1 with the seal cap detached from the retractor.
Figure 3:
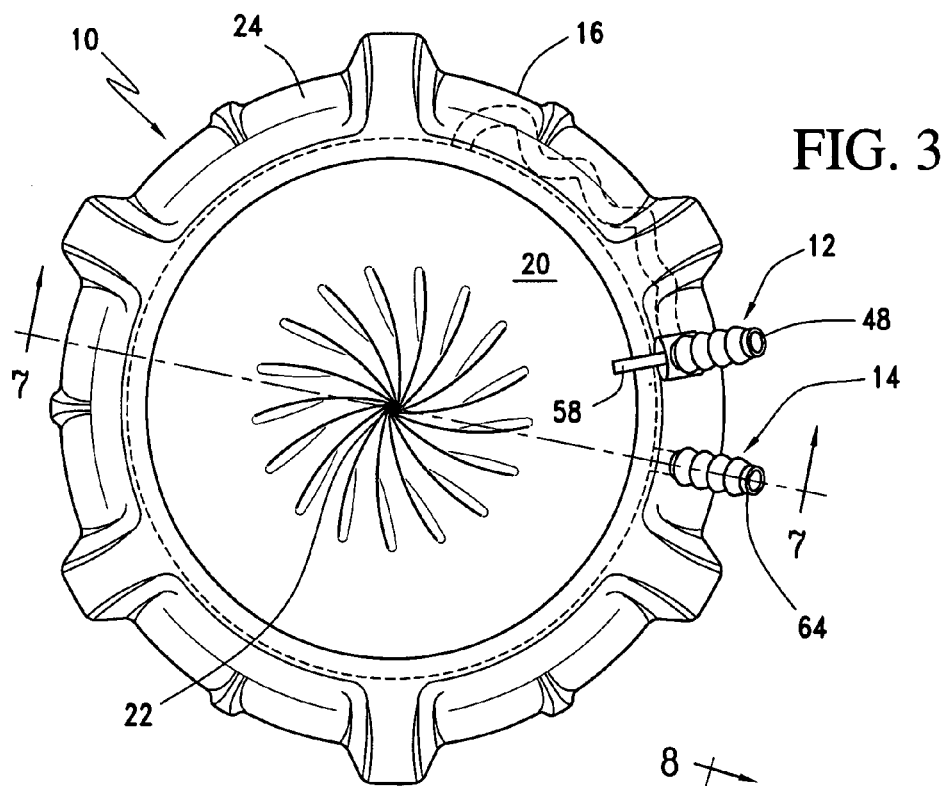
FIGS. 3 and 4 respectively show the iris seal in its closed orientation and open orientation.
Figure 4:
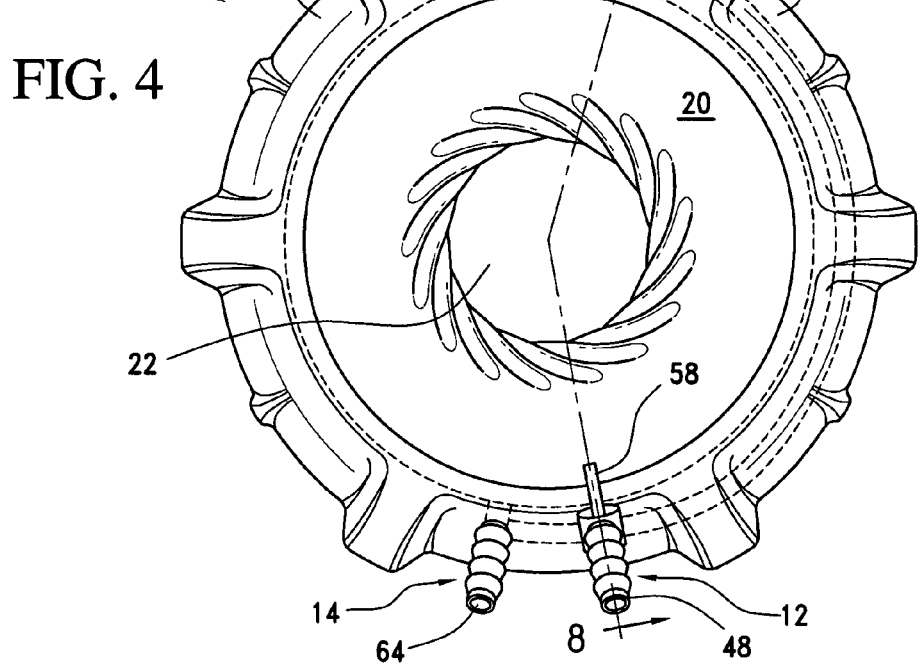

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as a basis for teaching one skilled in the art how to make and/or use the invention.

Referring to FIGS. 1 to 8, various devices for enhancing the functionality of a conventional laparoscopic seal assembly, or HALS seal assembly, 10 are disclosed. As those skilled in the art will certainly appreciate, laparoscopic seal assemblies are commonly employed during laparoscopic procedures and may take a variety of forms. For example, and in accordance with a preferred embodiment, a laparoscopic seal assembly as disclosed in commonly owned U.S. patent application Ser. No. 11/714,267, entitled "HAND ASSISTED LAPAROSCOPIC SEAL ASSEMBLY WITH A RATCHET MECHANISM", filed Mar. 6, 2007, is incorporated herein by reference.

As described below in greater detail, the present seal assembly 10 is designed in a manner permitting the incorporation of various devices for utilization in conjunction with the traditional functions of the seal assembly 10. With this in mind, the seal assembly 10 includes a series of manifold connections 12, 14 adapted to facilitate the additional functionalities contemplated in accordance with the present invention. In accordance with a preferred embodiment, it is contemplated the first and second manifold connections 12, 14 provide for the application of light (either visible or non-visible), vacuum, pressurized gas, energy in various forms (for example, RF or ultrasound), irrigation, ports or articulated links, cables and bands (such as, guidewires, retractors/probes, graspers or any functional device, biopsy devices and imaging devices).

Referring to the FIGS. 1 to 8, and in accordance with a preferred embodiment of the present invention, the seal assembly 10 generally includes an iris seal cap 16 and retractor 18 to ensure abdominal pressure is not compromised during hand exchanges while hand assisted laparoscopic procedures are performed. In accordance with a preferred embodiment of the present invention, the seal assembly 10 includes an iris seal 20 housed within a seal cap 16. The seal cap 16 is generally composed of an upper seal ring 26 and a lower seal ring 28 coupled for relative rotational movement. The iris seal 20 is mounted between the upper seal ring 26 and the lower seal ring 28 for movement between an open configuration and a closed configuration. The iris seal 20 includes a central access opening 22 allowing access to the body cavity as desired by the surgeon, or other medical practitioner, performing the procedure. As a result, the iris seal 20 is shaped and dimensioned to create a gas tight barrier around the surgeon's wrist when inserted through the seal assembly 10 and also creates a gas tight barrier between the interior abdominal space and the external environment when a hand is not inserted through the seal assembly 10. As will be discussed below in greater detail, adjustment of the iris seal 20, and ultimately the central access opening 22, provides for access to the body cavity in a highly controlled manner. As those skilled in the art will certainly appreciate, a variety of seal structures, other than an iris seal, are known and may be employed in accordance with the present invention without departing from the spirit of the present invention.

Referring to the various figures, the seal cap 16 includes an iris seal 20 positioned within a housing 24. As briefly mentioned above, the housing 24 includes an upper seal ring 26 and a lower seal ring 28 coupled together for relative rotational movement with the iris seal 20 positioned therebetween. The upper seal ring 26 and lower seal ring 28 are also coupled (as well as the iris seal 20) for relative rotational movement in a manner permitting opening and closing the iris seal 20 in a controlled manner. The housing 24 is made of soft textured material such as the thermoplastic elastomer SANTOPRENE, or other like materials, and supports the iris seal 20 in a concentric manner. Although SANTOPRENE is disclosed in accordance with a preferred embodiment, other housing materials may be used without departing from the spirit of the present invention.

As with prior hand assisted laparoscopic seal assemblies, the housing 24 of the present seal assembly 10 is secured to the abdominal wall of an individual patient by first creating an incision and positioning the retractor 18 and the seal cap 16 above the incision. Thereafter, the retractor 18, which will eventually be coupled to the seal cap 16, is inserted into the body cavity with the abdominal wall therebetween. The seal cap 16 is then connected to the retractor 18 in a manner securely connecting and supporting the seal cap 16 on the outside of the abdominal wall with the abdominal wall resiliently held between the retractor 18 and the seal cap 16.

More particularly, the surgical site is prepared in accordance with conventional standard hospital procedures, making sure the skin is clean and dry. Thereafter, a template is placed over the incision site and an incision line is marked upon the template using a sterile skin marker. As those skilled in the art will appreciate, the glove size dictates the size of the incision. For example, if the surgeon's glove size is 7, a 6.5 to 7.0 cm incision is usually appropriate. Thereafter, an incision is made along the marked incision line. The incision size is thereafter verified by inserting the surgeon's hand into the abdomen prior to installing the retractor 18 and the present seal assembly 10. If the incision is too small, the incision is extended as required on each end to maintain the central position of the incision relative to the placement of the retractor 18 and the present seal assembly 10. Thereafter, the lower retractor ring 30 of the retractor 18 is inserted through the incision. Using one's fingers, the lower retractor ring 30 is seated evenly under the peritoneum and the area is swept to ensure the retractor 18 is not lying between tissue layers. Thereafter, the seal cap 16 is attached to the retractor 18 via an attachment ring 32, which may be rigid but not limited thereto, and adjustments are made to ensure the seal assembly 10 is secured with the patient's abdomen, maintaining pneumo. As those skilled in the art will certainly appreciate, the retractor 18 may be a fixed length or adjustable length retractor. In either case the retractor 18 must fit the abdominal wall thickness to maintain stability and pneumo. As briefly discussed above, the present seal assembly 10 is provided with an attachment ring 32 that is detachable from the remaining portions of the housing 24 for permitting selective attachment of the retractor 18 to the present seal cap 16.

In accordance with a preferred embodiment of the present invention, the attachment ring 32 is substantially the same as those disclosed in commonly owned U.S. patent application Ser. No. 11/730,922, entitled "HAND ASSISTED LAPAROSCOPIC SEAL ASSEMBLY WITH DETACHABLE ATTACHMENT RING", filed Apr. 4, 2007, which is incorporated herein by reference. However, and as those skilled in the art will certainly appreciate, other retractor attachment techniques may be employed without departing from the spirit of the present invention.

As briefly mentioned above, the seal cap 16 of the seal assembly 10 is utilized as a manifold for supporting various functional apparatuses and accordingly includes the first and second manifold connections 12, 14. Although two manifold connections are disclosed herein in accordance with a preferred embodiment of the present invention, those skilled in the art will appreciate the number of manifold connections may be varied to suit specific needs without departing from the spirit of the present invention.

A finger-mounted tether 34 for HALS applications is connected to the second manifold connection 14. In accordance with a preferred embodiment, the finger-mounted tether 34 includes a finger base platform 42. More particularly, the finger base platform 42 is composed of a resilient finger-attachment member 44. The resilient finger-attachment member 44 is substantially circular shaped and includes an expansion cut 66 permitting the finger-attachment member 44 to expand and contract to fit different finger sizes. Although a resilient finger-attachment member is disclosed in accordance with a preferred embodiment of the present invention, the finger-attachment member may take various forms, for example, a deflection member, a strap with a catch, or a rigid tapered thimble, without departing from the spirit of the present invention. An accessory attachment recess 68 is formed along the outer wall of the finger-attachment member 44. As a result, the finger-attachment member 44 may be selectively attached to various functional components which may be secured at the distal end of the finger-mounted tether 34.

Figure 5:
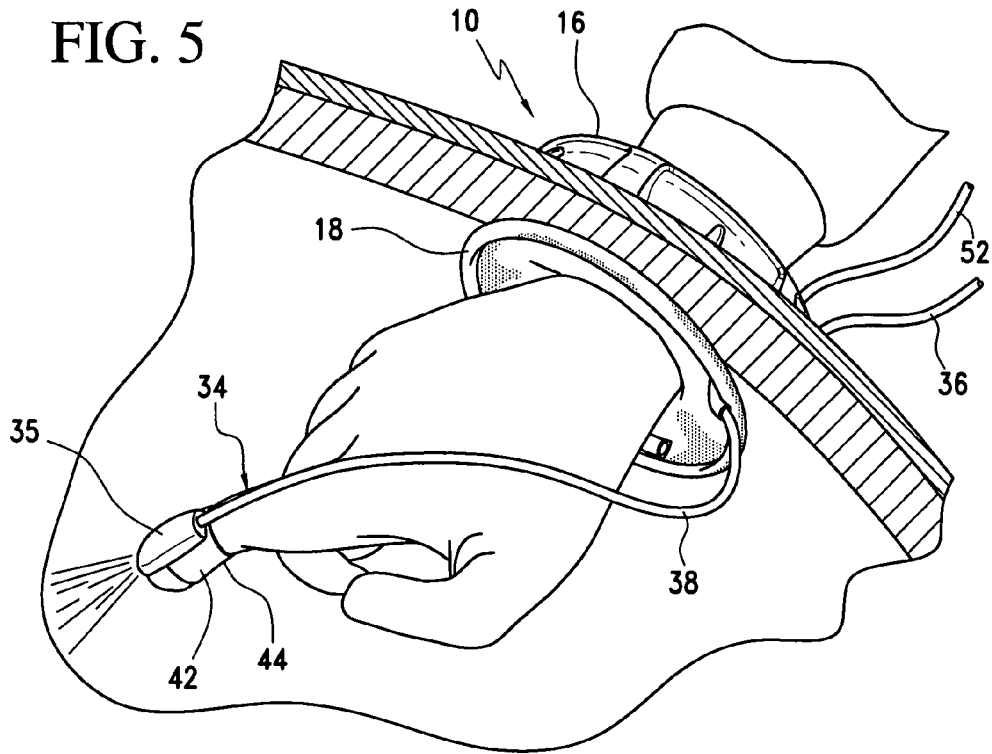
FIGS. 5 and 6 show the finger-mounted catheter/tether in accordance with alternate embodiments.
Figure 6:
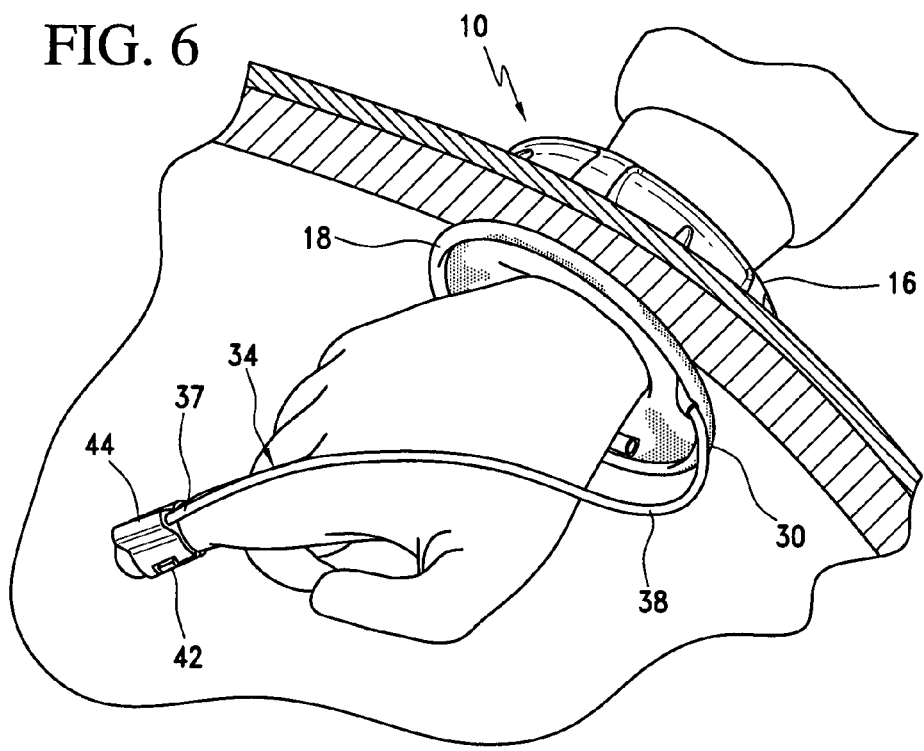
Figure 7:
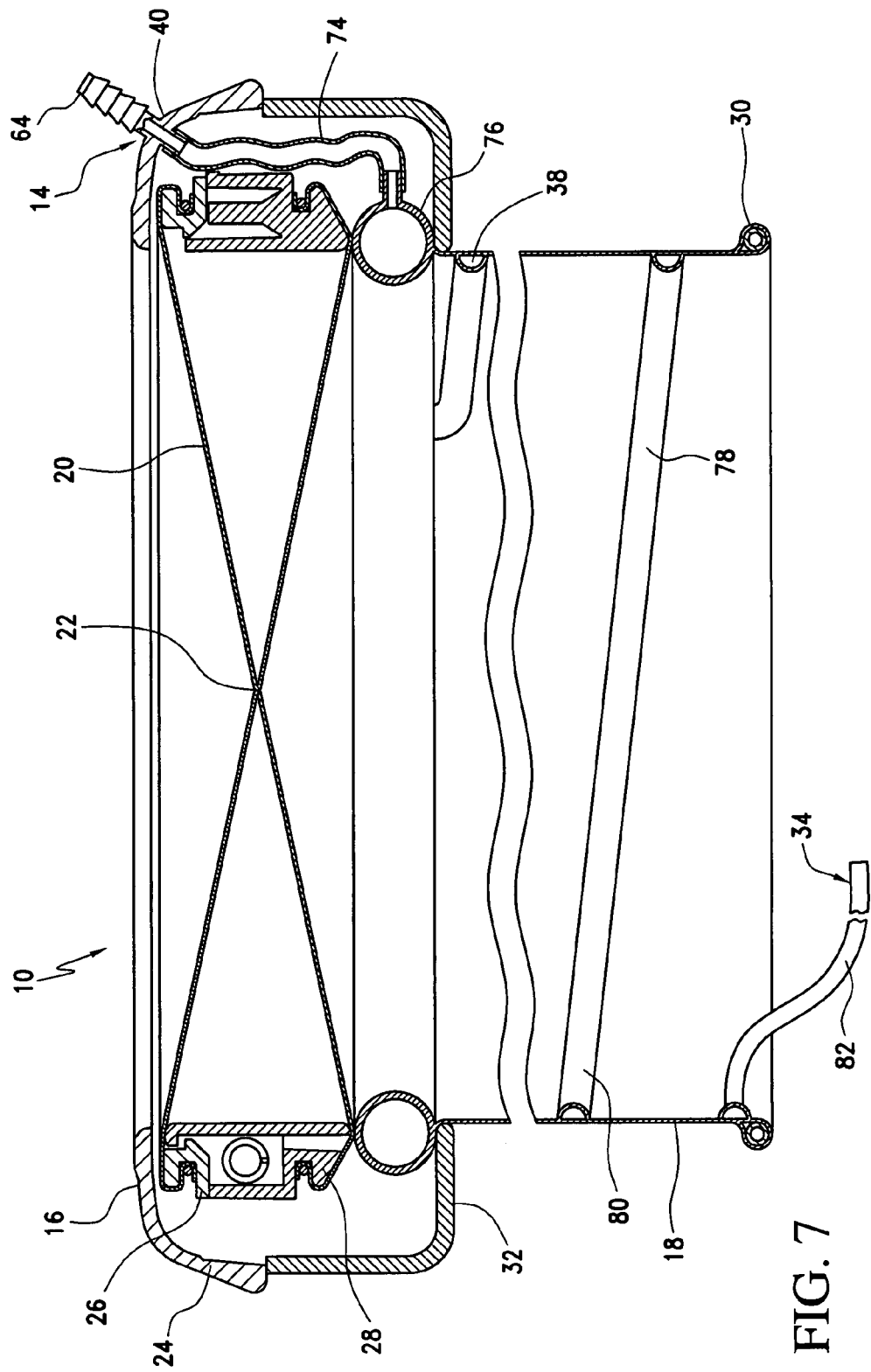
FIG. 7 is a cross sectional view along the line 7-7 in FIG. 3
Figure 8:
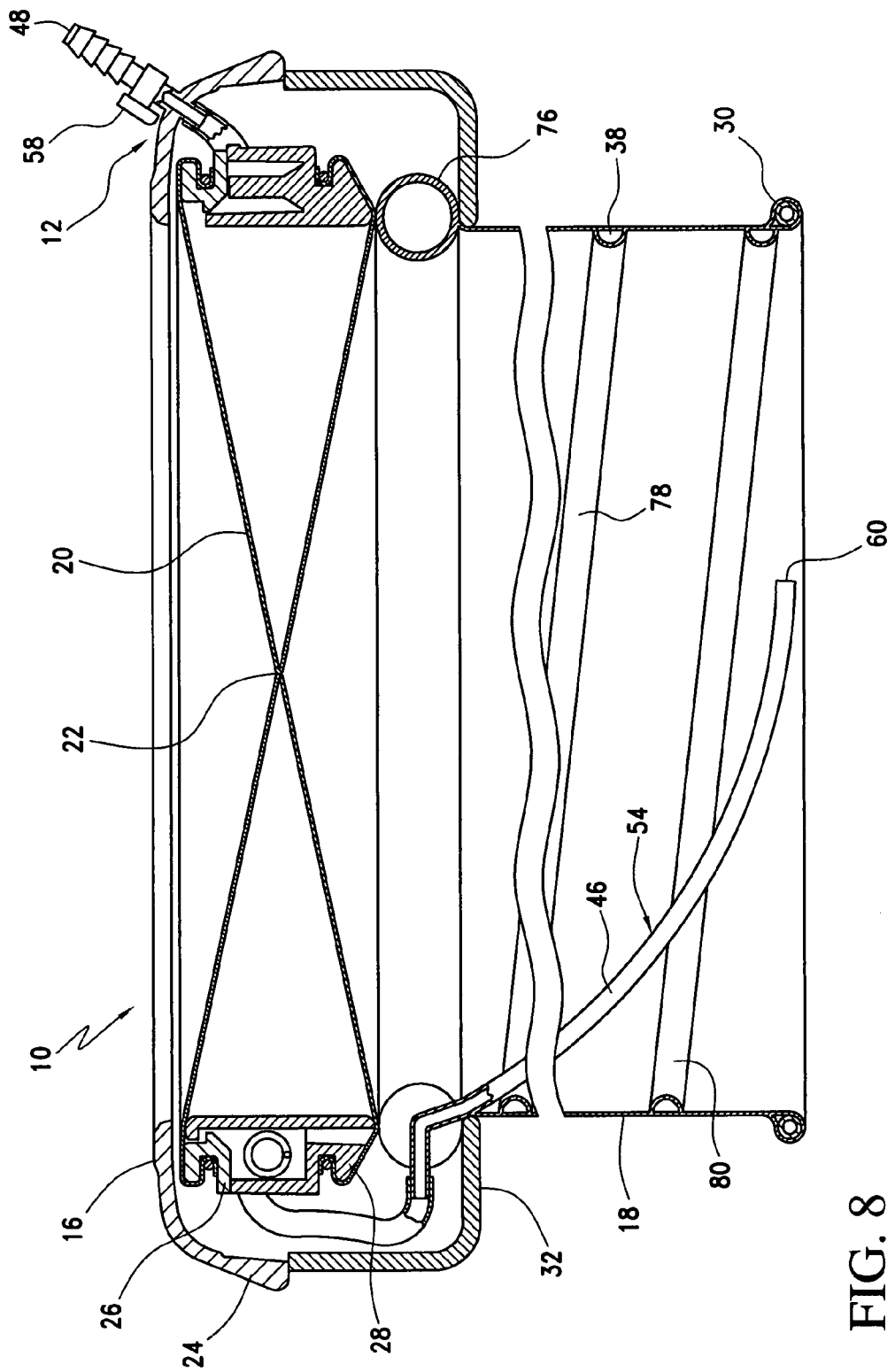
FIG. 8 is a cross sectional view along the line 8-8 in FIG. 4.
Figure 9:
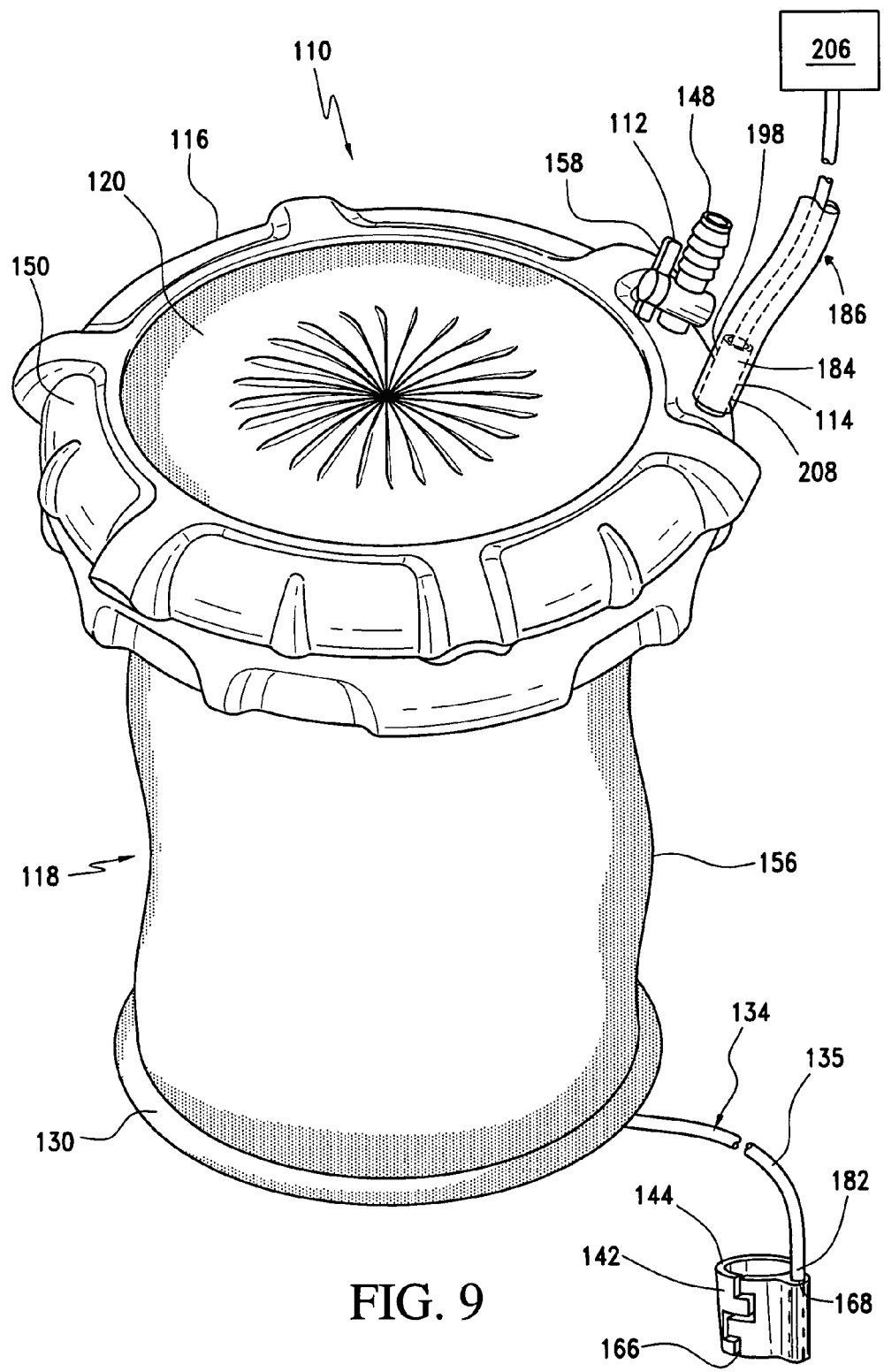
FIG. 9 is a perspective view of a laparoscopic seal assembly in accordance with an alternate embodiment.
Figure 10:
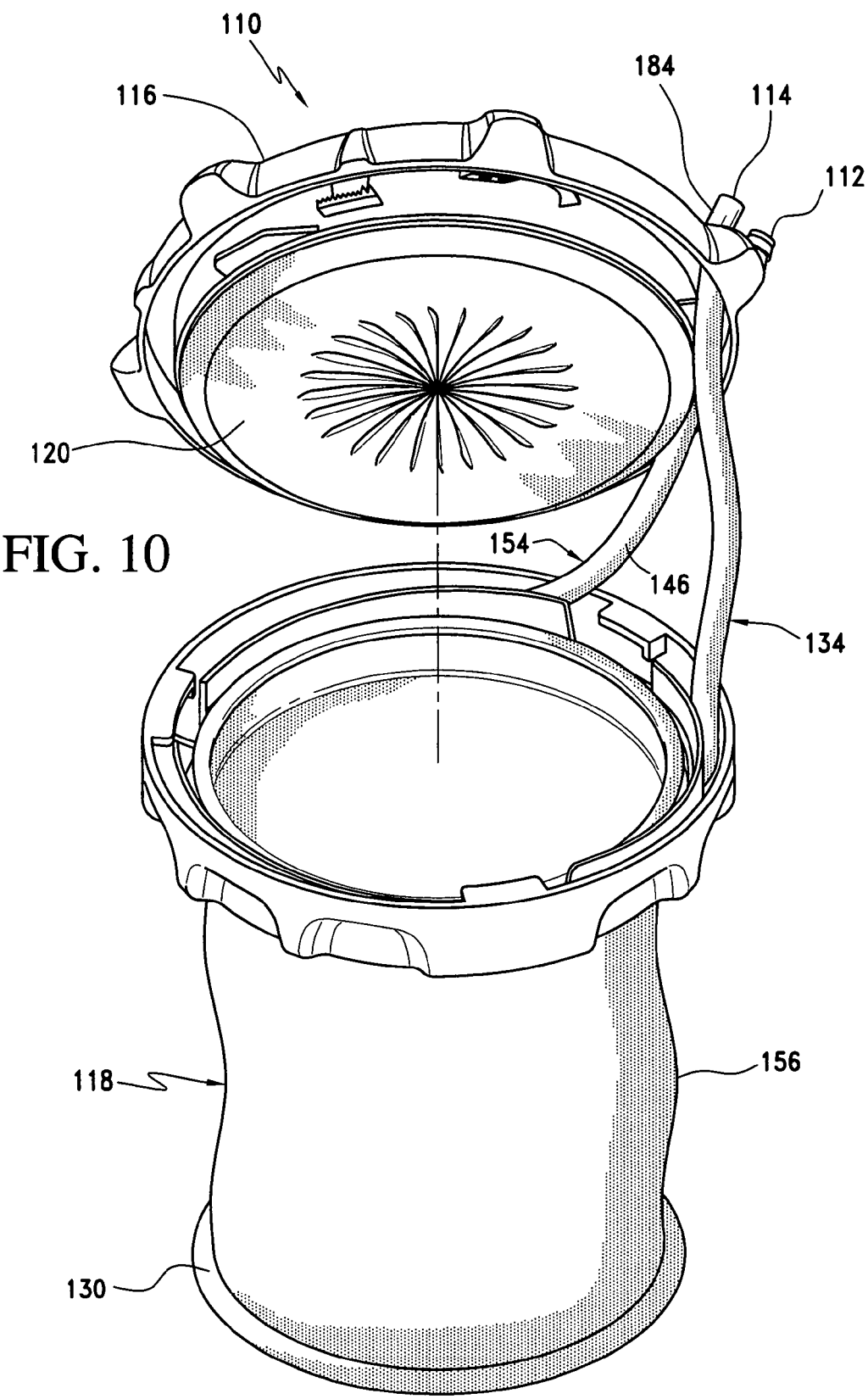
FIG. 10 is a perspective view of the laparoscopic seal assembly shown in FIG. 9 with the seal cap detached from the retractor.
Figure 11:
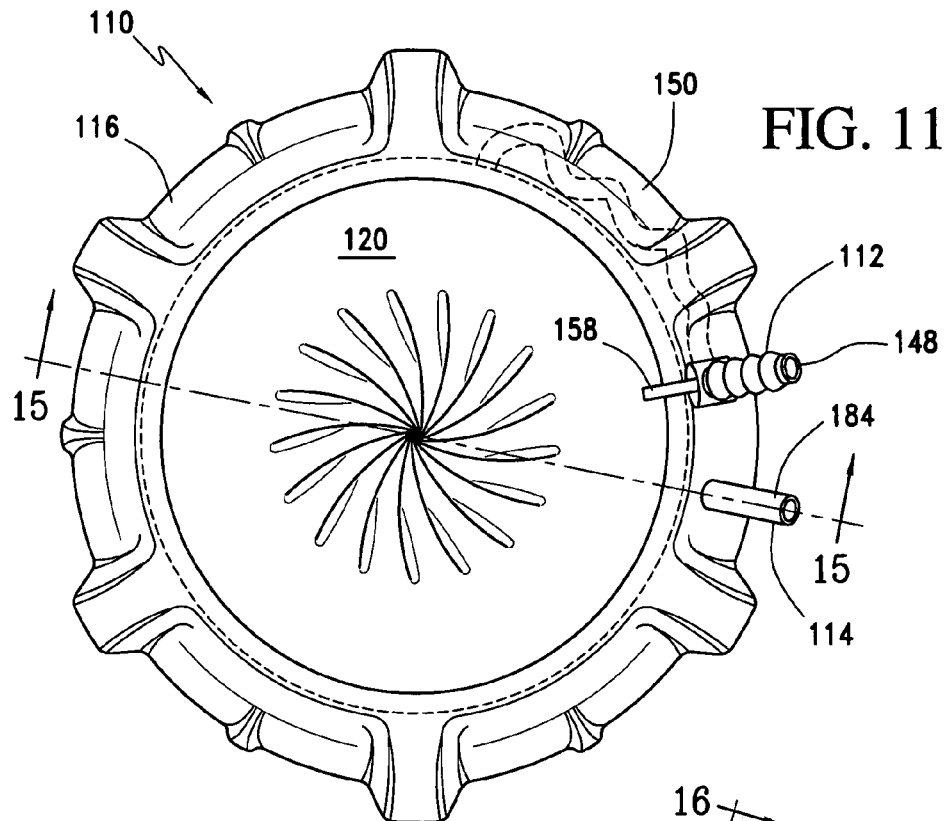
FIGS. 11 and 12 respectively show the iris seal in its closed orientation and open orientation.
Figure 12:
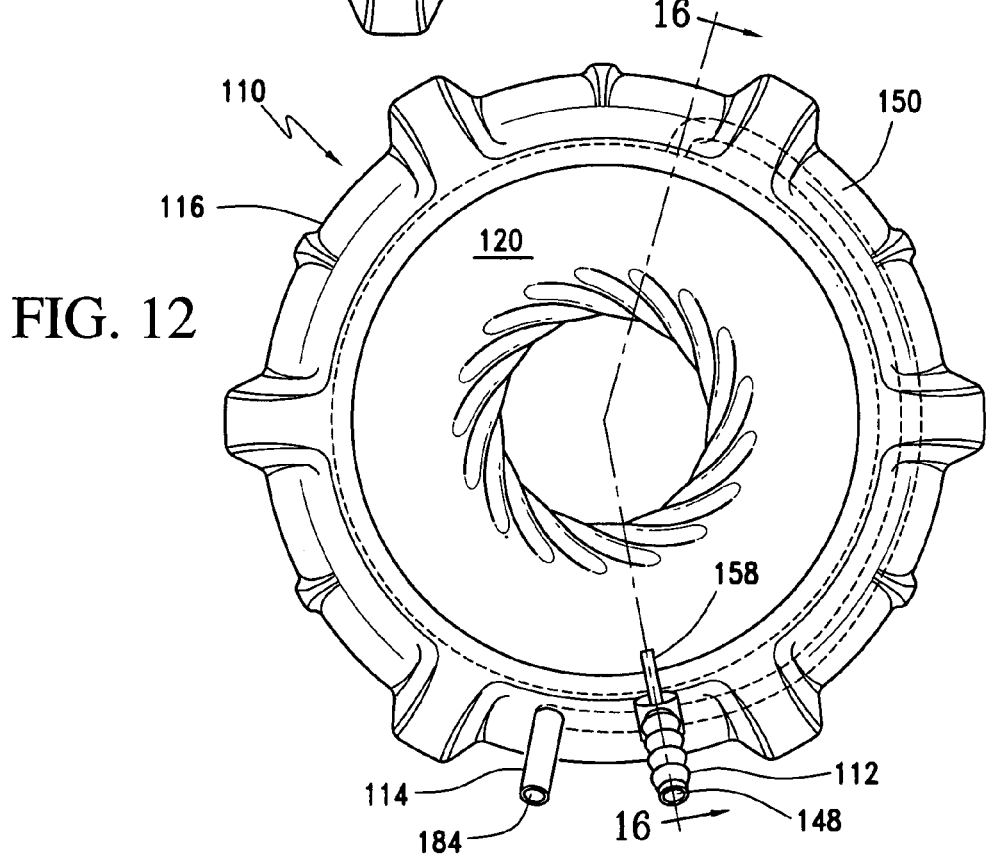

As shown with reference to FIGS. 5 and 6, the finger-mounted tether 34 may be employed in bringing light, or another energy source, 35 (see FIG. 5) or a fluid port 37 (FIG. 6) into the abdominal cavity. In the case where the finger-mounted tether 34 is intended to transport fluid or other medium, for example, as shown with reference to FIG. 6, it will be formed with a lumen and structured to resemble a catheter. The tether 34 can be manipulated to dry tissue in circumstances where it is desired to apply an adhesive. The dried tissue will result in better adhesion.

The finger-mounted tether 34 includes a proximal portion 36 and a distal portion 38, and is connected to the second manifold connection 14 via a conventional hollow nipple arrangement 64. The proximal portion 36 of the finger-mounted tether 34 is external to the seal cap 16 and is connected thereto via a nipple arrangement 64. In accordance with a preferred embodiment of the present invention, the proximal portion 36 is preferably approximately 15.2 cm long (for example, where it is to be connected to other tubing extensions) to approximately 25.4 cm long (for example, where it is to be connected to room inputs), and more preferably, the proximal portion 36 is approximately 68.6 cm to approximately 91.4 cm long. However, those skilled in the art will appreciate the length of the proximal portion may be varied to suit specific needs.

In accordance with a preferred embodiment, a first end 70 of the proximal portion 36 of the finger-mounted tether 34 is connected in an extra-corporeal fashion to a syringe plunger, power source or similar mechanism 72 for the application of desired treatment within the body cavity. In accordance with a preferred embodiment, the finger-mounted tether 34 may be connected to a coagulant or fibrin glue source permitting the introduction of biosurgical materials such as fibrin glue for sealing tissue leaks (pneumo/blood) and/or adhesive for bonding of edges/anastomosis, anti-adhesion substances. By providing a mechanism for introducing these materials the present invention is able to save steps and ultimately time, by permitting direct application at one's fingertip.

The distal portion 38 of the finger-mounted tether 34 is coupled to the internal side of the nipple arrangement 64 and extends through the seal assembly 10 for utilization during HALS procedures. Those skilled in the art will appreciate that various configurations are possible within the spirit of the present invention. For example, and with reference to FIG. 7, a tubing member 74 connects the nipple arrangement 64 to a hollow ring, which also functions as the upper retractor ring 76. The tubing member 74 is provided with sufficient slack to allow for rotation of the seal assembly 10 in a manner known to those skilled in the art. The hollow ring 76 is integrally formed with the retractor 18 and functions as a manifold with connecting spiral tubing 78 extending therefrom so as to define the distal portion 38 of the finger-mounted tether 34. In accordance with such an embodiment, the upper end 80 of the distal portion 38 of the finger-mounted tether 34 is integrally formed with the retractor 18 and the free end 82 of the distal portion 38 extends beyond the retractor 18 for actuation in accordance with the present invention. In accordance with alternate embodiments, it is contemplated a spiral tube with bypassing rings may be employed, a spiral tube integral into wall or attached to wall may be used, multiple tubes or paths may be employed. The spiral structure allows the tubing to have the flexibility for changing radial or ring compression forces without being highly stressed.

The specific functionality of the finger-mounted tether 34 may be varied to suit specific applications. For example, where there is not a need for the lumen of a catheter, it may simply take the form of a tether to assist with, for example, intra-abdominal instrument storage while the device is not in use. The catheter instrument could also be used as a suction/irrigation device to assist with bleeding management. In addition, the number of hand exchanges encountered in the utilization of a HALS access device may be reduced by utilizing an energy port in conjunction with the finger-mounted tether. Regardless of the source or type of energy, which may be light, optical, ultrasound, Doppler, ultrasonic, RF, microwave, or any other energy commonly found in the operating room environment, the energy port provides a mechanism for transferring the energy to the operative site under minimally invasive surgical procedure insufflation.

In accordance with a preferred embodiment, the finger-mounted tether 34 may be formed integrally with the HALS seal assembly 10 so as to not interfere with the function of the HALS seal assembly 10, but provide a safe passageway into the abdominal cavity. The finger-mounted tether 34 is passed through a port 40 formed within the seal cap 16.

As discussed above, the finger-mounted tether 34 includes a finger base platform 42 at the free end 82 of the distal portion 38 thereof for attachment to the finger of an individual performing a medical procedure. As discussed above, the free end of tether 34 can be manipulated to direct the flow (for example, energy, fluid or gas) exiting tether 34. In accordance with a preferred embodiment, the finger base platform 42 is a resilient finger-attachment member 44 that will frictionally engage the tip of an individual's finger for manipulation within the body under the control of a medical practitioner's hand. Although a resilient attachment member as described above is disclosed in accordance with a preferred embodiment of the present invention, it is contemplated the attachment mechanism may take the form of a deflection member, a strap with a catch, or another structure permitting secure attachment to a user's finger.

Those skilled in the art will certainly appreciate the finger-mounted tether 34 disclosed in accordance with the present invention may have uses beyond that of the seal assembly 10 in which it is disclosed. For example, it is contemplated the present finger mounted catheter/tether may be an independent tube to be used for a functional purpose such as with a duck bill valve to prevent infusion gas ($CO_2$) from escaping such as for irrigation. This is in addition to the directly connected device (as illustrated) or assembleable device for connection once in the body cavity (having the appropriate connections as referenced). There may be one or more connection points to operate the variety of potential device use.

As those skilled in the art will certainly appreciate, a number of surgical steps are required for set up of a minimally invasive surgical procedure. As such, a mechanism for reducing the number of surgical steps employed during the set up of a minimally invasive surgical procedure is disclosed. This is achieved through incorporation of a $CO_2$ insufflation passageway 46 into the seal assembly 10. As a result, insufflation $CO_2$ is transferred into the abdominal cavity by way of circular patterns following the natural shape of the seal assembly 10. Through the utilization of tubing, stability is provided to the incision site by providing a surface conducive to prevent slippage and rotation.

An input port 48 is located on the external side 50 of the seal cap 16 of the HALS seal assembly 10. External tubing 52 links the input port 48 to a gas source (not shown). The input port 48 is in fluid communication with a lumen 54 integrally formed with the seal cap 16, the retractor body 56 and the lower retractor ring 30. The lumen is integrally formed with the wall of the retractor 18 as shown with reference to FIG. 8. The lumen 54 extends from the input port 48 to the exit port 60 thereof at the lower retractor ring 30 of the retractor 18. A stopcock valve 58 is integrated with the input port 48 for controlling the flow of gas through the seal cap 16, the retractor body 56 and the lower retractor ring 30.

The lumen 54 ends in an exit port 60 that is in fluid communication with the abdominal cavity when the seal assembly 10 is properly positioned within an individual's incision. The exit port 60 is oriented to supply gas to the abdominal cavity in a manner creating a circular pattern following the natural shape of the laparoscopic seal assembly. The orientation of the exit port 60 is ultimately feature dependent. In addition to creating gas flow following the shape of the seal cap 16, the orientation of the exit port 60 provides flexibility flow stress) for tubing/wires. In addition, holes in the insufflation passageway would allow for gentler non-directional $CO_2$ insufflation to avoid drying tissue affected by a direct air stream or a direct stream from a tube would allow drying an area for biosurgical application if needed. As a result of the insufflation stopcock valve 58, it is contemplated a gas source may be linked to the input port 48 and placed in fluid communication with the abdominal cavity via the lumen 54 and the exit port 60.

In accordance with an alternate embodiment, and with reference to FIGS. 9 to 16, a modular construction is disclosed. As with the prior embodiment, the seal cap 116 of the seal assembly 110 is utilized as a manifold for supporting various functional apparatuses and accordingly includes first and second manifold connections 112, 114. However, and in contrast to the embodiment described above, the present embodiment allows for selective attachment of various functional components to permit utilization of the present seal assembly 110 in a variety of environments. Although two manifold connections are disclosed herein in accordance with a preferred embodiment of the present invention, those skilled in the art will appreciate, the number of manifold connections may be varied to suit specific needs without departing from the spirit of the present invention.

As with the prior embodiment, the first manifold connection 112 is adapted for permitting insufflation. More particularly, the first manifold connection 112 forms part of a $CO_2$ insufflation passageway 146 in the seal assembly 110. As a result, insufflation $CO_2$ is transferred into the abdominal cavity by ways of circular patterns following the natural shape of the seal assembly 110.

As with the prior embodiment, an input port 148 is located on the external side 150 of the seal cap 116 of the HALS seal assembly 110. External tubing 152 links the input port 148 to a gas source (not shown). The input port 148 is in fluid communication with a lumen 154 integrally formed with the seal cap 116, the retractor body 156 and the lower retractor ring 130. The lumen 154 is integrally formed with the wall of the retractor 118 as shown with reference to FIG. 16. The lumen 154 extends from the input port 148 to the exit port 160 thereof at the lower retractor ring 130 of the retractor 118. A stopcock valve 158 is integrated with the input port 148 for controlling the flow of gas through the seal cap 116, the retractor body 156 and the lower retractor ring 130.

The lumen 154 ends in an exit port 160 which is in fluid communication with the abdominal cavity when the seal assembly 110 is properly positioned within an individual's incision. The exit port 160 is oriented to supply gas to the abdominal cavity in a manner creating a circular pattern following the natural shape of the seal assembly 110.

With regard to the second manifold connection 114, it is adapted for attachment of various functional components, such as, energy sources or fluid ports. More particularly, it is contemplated the functional components may include a mechanism for the introduction of a coagulant or fibrin glue permitting the introduction of biosurgical materials such as fibrin glue for sealing tissue leaks (pneumo/blood) and/or adhesive for bonding of edges/anastomosis. The functional components may also include supply mechanisms for anti-adhesion substances or an intra-abdominal instrument storage functionality for instruments while they are not in use. Additional functional components may include suction/irrigation devices to assist with bleeding management or an energy port for internal application of energy as required for various surgical procedures. Regardless of the source or type of energy, which may be light, optical, ultrasound, Doppler, ultrasonic, RF, or any other energy commonly found in the operating room environment, the energy port provides a mechanism for transferring the energy to the operative site under minimally invasive surgical procedure insufflation.

With the foregoing in mind, the second manifold connection 114 includes an external port 184 for selective connection to a external supply source 186, whether it is a fluid source, vacuum source, gas source, energy source, etc. The second manifold connection 114 also includes an internal port 188 formed within the seal assembly 110, that is, beneath the seal 120 and within the passageway defined by the seal assembly 110. The internal port 188 is adapted for selective attachment of a finger-mounted tether 134 for HALS applications. As with the prior embodiment, the finger-mounted tether 134 includes a flexible linking member 135 with a finger base platform 142 at a free end 182 thereof. More particularly, the finger base platform 142 is composed of a resilient finger-attachment member 144. The resilient finger-attachment member 144 is substantially circular shaped and includes an expansion cut 166 permitting the finger-attachment member 144 to expand and contract to fit different finger sizes. An accessory attachment recess 168 is formed along the outer wall of the finger-attachment member 144. As a result, the finger-attachment member 144 may be selectively attached to various functional components that may be secured at the free end 182 of the finger-mounted tether 134.

As those skilled in the art will certainly appreciate the seal assembly 110 includes a rotational mechanism allowing selective rotation of the upper seal ring 126 to which the external port 184 is connected and the lower seal ring 128 to which the internal port 188 is connected. A tubing member 190 housed within the seal assembly 110 connects the external port 184 and the internal port 188, and the tubing member 190 is provided with sufficient slack to permit movement of the upper seal ring 126 relative to the lower seal ring 128.

In order to provide for the connection of multiple external sources and multiple functional finger-mounted tethers to the second manifold connection 114, the second manifold connection 114 and tubing member 190 are provided with multiple conductive elements 192, 194, 196 permitting transfer between the external port 184 and the internal port 188. In particular, and in accordance with a preferred embodiment of the present invention, the second manifold connection 114 includes a lumen 192 for fluid or gas transfer, a fiber optic connection 194 and an electrical connection 196. The conductive elements 192, 194, 196 respectively align with the external supply source 186 at the external port 184 and the finger-mounted tether 134 at the internal port 188 to permit selective transfer through the second manifold connection 114 and between the external and internal ports 184, 188.

With this in mind, the external port 184 and the internal port 188 are provided with connection members 198, 200 allowing for selective functional connection of the respective external supply source 186 and finger-mounted tether 134.

Figure 13:
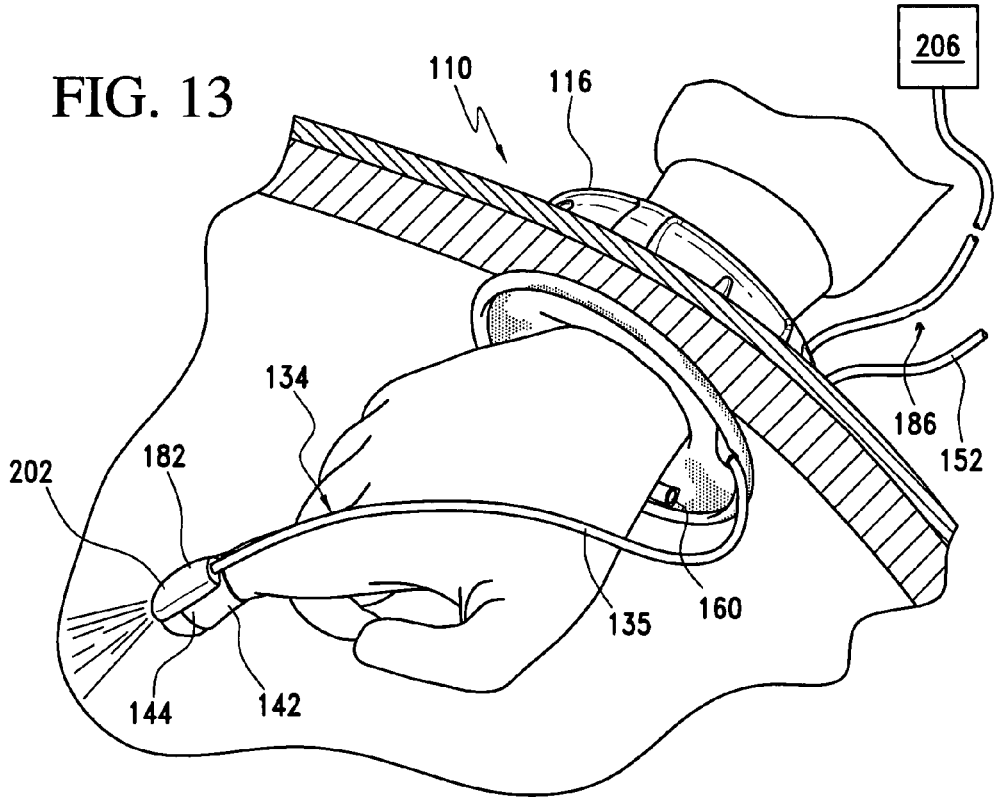
FIGS. 13 and 14 show the finger-mounted catheter/tether in accordance with alternate embodiments.
Figure 14:
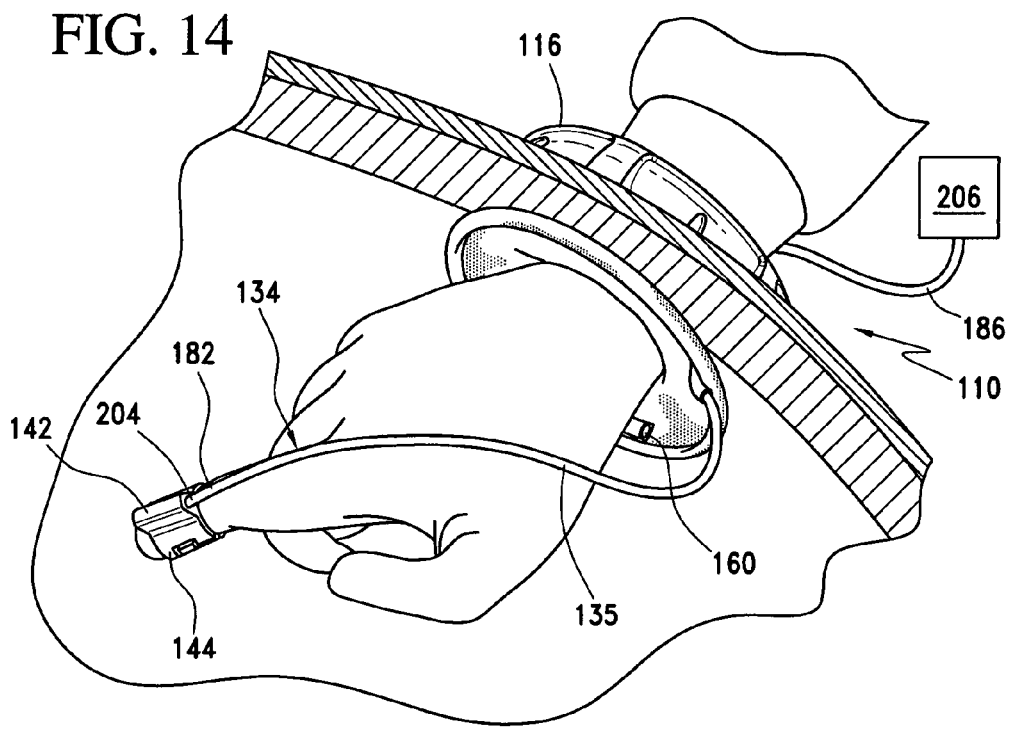
Figure 15:
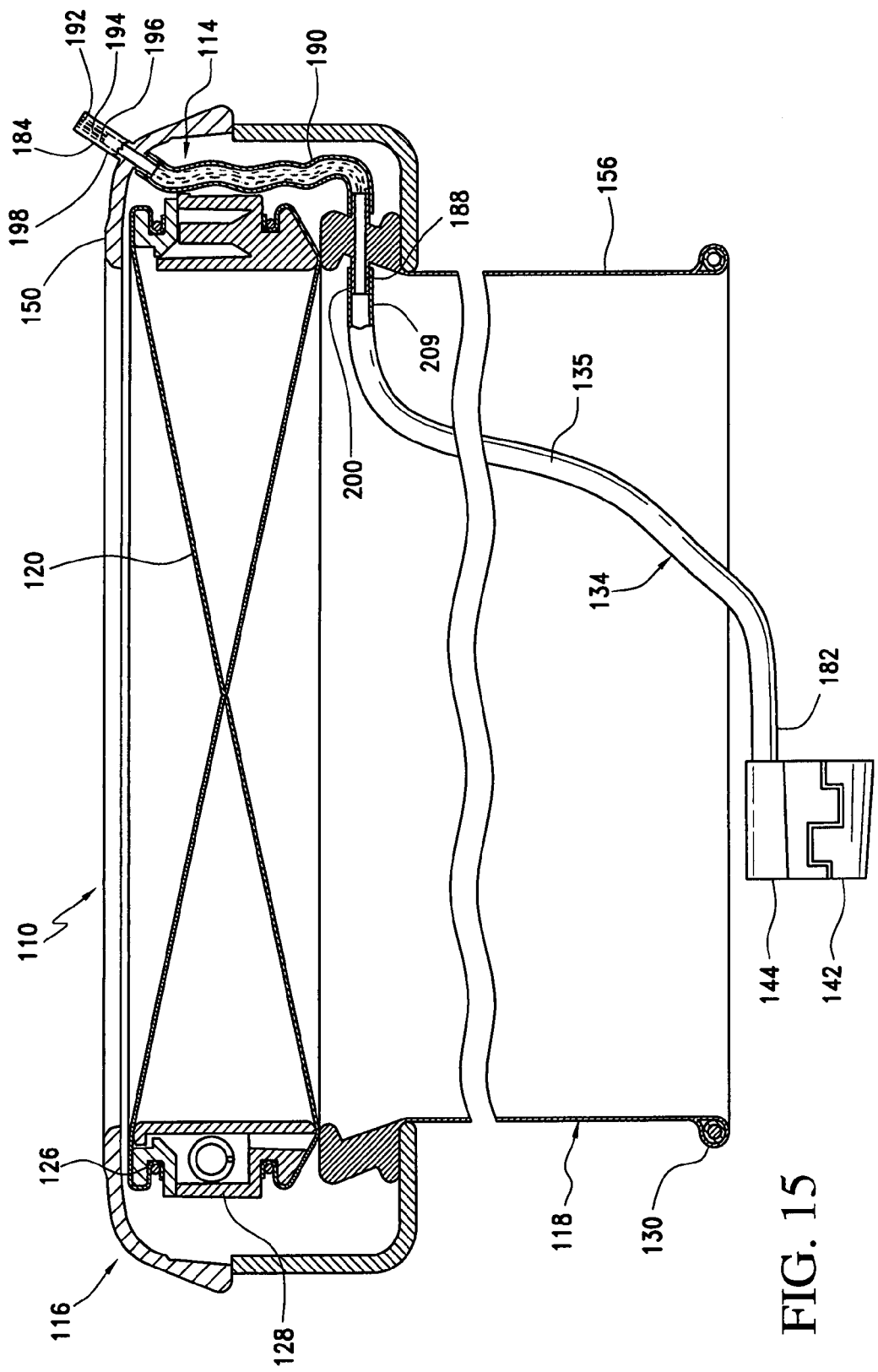
FIG. 15 is a cross sectional view along the line 15-15 in FIG. 11.
Figure 16:
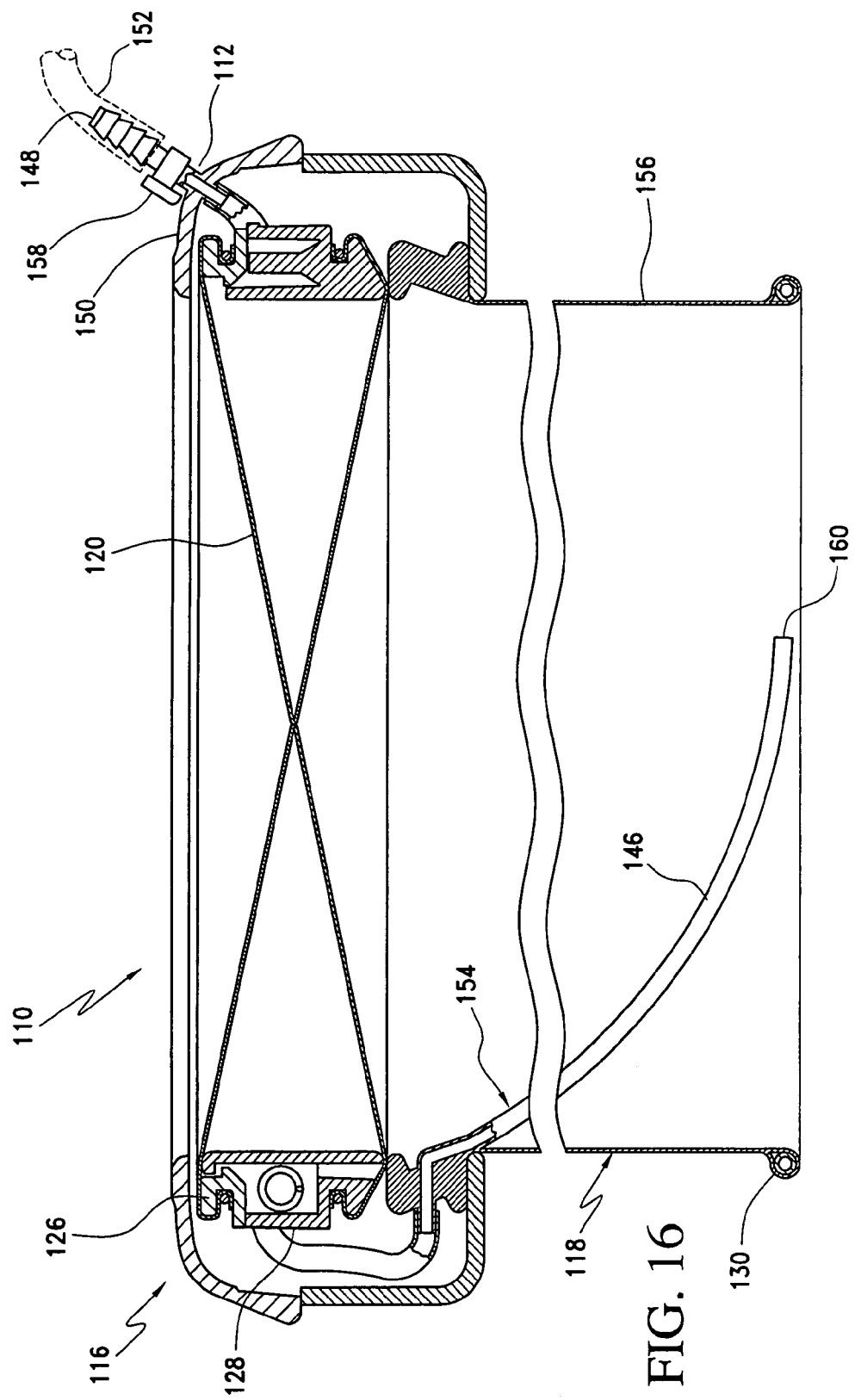
FIG. 16 is a cross sectional view along the line 16-16 in FIG. 12.

As shown in FIG. 13, the external supply source 186 may be a light source that is ultimately connected to a finger-mounted tether 134 provided with a light member 202. Similarly, and with reference to FIG. 6, the external supply source 186 may be a fluid source that is ultimately connected to a finger-mounted tether 134 provided with a lumen 204 for the transport fluid to a predetermined body site.

In accordance with a preferred embodiment, the external supply source 186 includes a proximal portion to which a supply member 206 (for example, energy supply, fluid supply, gas supply) is attached and a distal portion having a connection member 208 shaped and dimensioned for selective connection with the connection member 198 of the external port 184 of the second manifold connection 114.

The finger-mounted tether 134 also includes a distal portion and a proximal portion. The proximal portion is provided with a connection member 209 for selective connection with the internal port 188 of the second manifold connection 114. The distal portion of the finger-mounted tether 134 includes a free end 182 that is coupled to the finger base platform 142 for attachment to the finger of an individual performing a medical procedure. In accordance with a preferred embodiment, the finger base platform 142 is a resilient finger-attachment member 144 that will frictionally engage the tip of an individual's finger for manipulation within the body under the control of a medical practitioner's hand.

Figure 17:
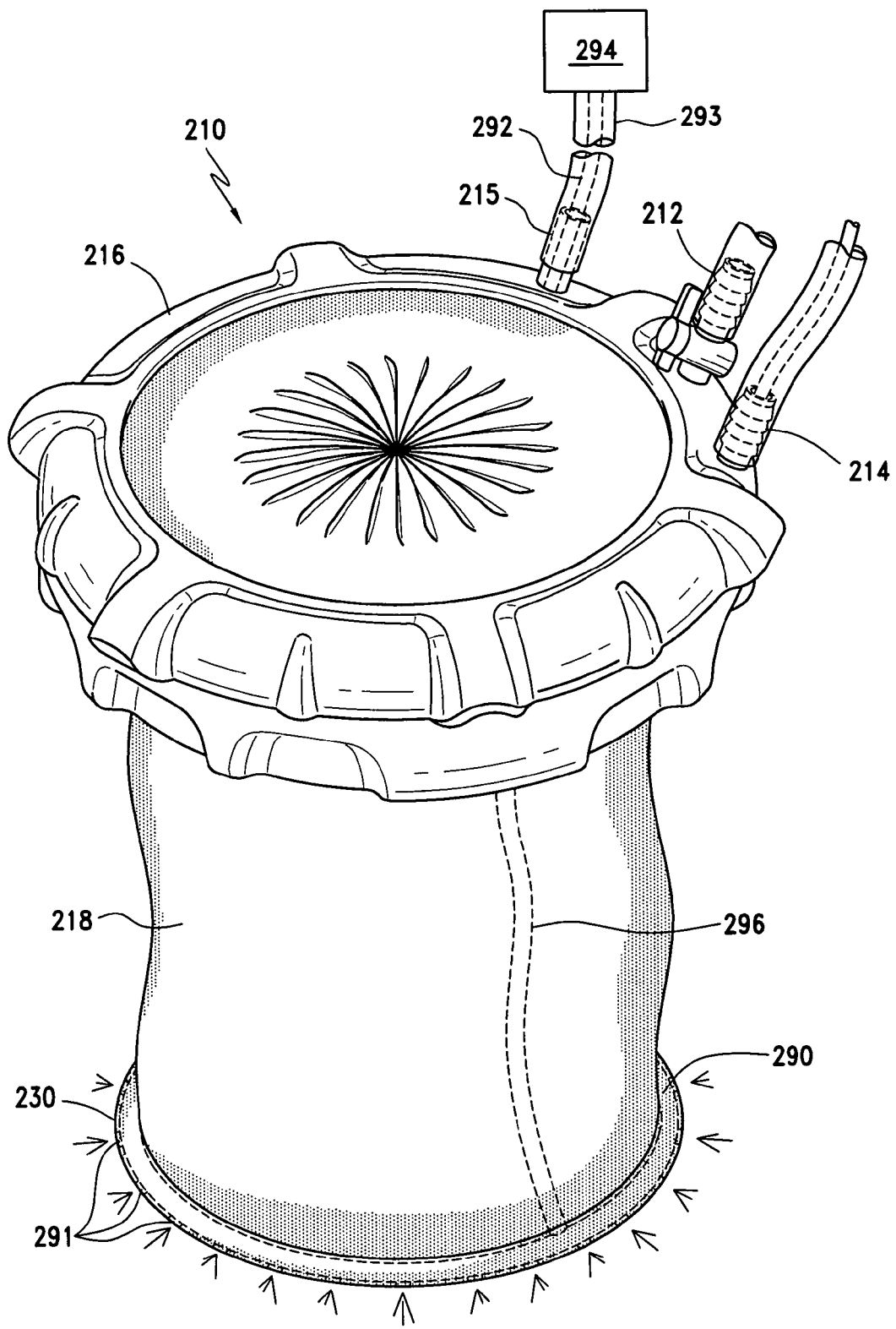
FIG. 17 is a perspective view of a laparoscopic seal assembly in accordance with another alternate embodiment.

As discussed above, the present seal assembly may be provided with additional manifold connections. For example, and with reference to FIG. 17, a seal assembly 210 is disclosed which includes first, second and third manifold connections 212, 214, 215. The first and second manifold connections 212, 214 are substantially the same as described above with reference to FIGS. 1-8.

The third manifold connection 215 is designed for linking a light source 294 to a light ring 290 incorporated into the lower retractor ring 230. In accordance with a preferred embodiment, the light ring 290 is a fiber optic cable. More particularly, a fiber optic cable 292 links a light source 294 to the third manifold connection 215, for the transmission of light from the light source 294 to the seal assembly 210. The third manifold connection 215 is then internally connected to the light ring 290 within the lower retractor ring 230 by an internal fiber optic cable 296 constructed to pass through the seal cap 216 and the retractor 218. As a result, light generated by the light source 294 may be transmitted to the light ring 290 for illuminating a body cavity. As those skilled in the art will certainly appreciate, the light ring 290 and the lower retractor ring 230 are constructed such that light is properly directed out of the light ring 290, through the lower retractor ring 230 and into the body cavity with a desired focus. This can be accomplished by spaced openings 291 in the lower retractor ring 230 or by manufacturing the lower retractor ring so as to be transparent or translucent so light can pass therethrough. Further, it is contemplated the lower retractor ring could be coupled with energy source 35 running through finger-mounted tether 34 as described with regard to FIG. 5.

It will be understood by those skilled in the art that any one or more of the following described embodiments, expressions of embodiments, examples, etc. can be combined with any or more of the other following described embodiments, expressions of embodiments, examples, etc.

While the preferred embodiments have been shown and described, it will be understood that there is no intent to limit the invention by such disclosure, but rather, is intended to cover all modifications and alternate constructions falling within the spirit and scope of the invention.

The invention claimed is:

1. A laparoscopic seal assembly, comprising:
   a finger-mounted tether;
   a seal cap including a seal having an access opening, the seal cap also including a manifold connection connected to the finger-mounted tether; and
   a retractor coupled to the seal cap;
   wherein the manifold connection includes a nipple arrangement through which a proximal portion of the finger-mounted tether passes and a distal portion of the finger mounted tether is coupled to and extends beyond the retractor.

2. The laparoscopic seal assembly according to claim 1, wherein the finger-mounted tether includes an accessory attachment recess for selective attachment of various functional components.

3. The laparoscopic seal assembly according to claim 1, wherein the finger-mounted tether includes an energy source.

4. The laparoscopic seal assembly according to claim 1, wherein the finger-mounted tether includes a fluid port.

5. The laparoscopic seal assembly according to claim 1, wherein the finger-mounted tether includes a finger-attachment mechanism.

6. The laparoscopic seal assembly according to claim 5, wherein the finger-attachment mechanism includes an elastomeric ring shaped and dimensioned to frictionally engage a finger.

7. The laparoscopic seal assembly according to claim 1, wherein the retractor includes a hollow upper retractor ring and a connecting spiral tubing extending through the retractor from the upper retractor ring to the lower retractor ring where the distal portion of the finger-mounted tether extends beyond the retractor.

8. The laparoscopic seal asssembly according to claim 7, wherein the hollow upper retractor ring and the connecting spiral tubing define a portion of the distal portion of the finger mounted tether.

9. A laparoscopic seal assembly, comprising:
a seal cap including a seal having an access opening, the seal cap includes a housing in which the seal is positioned, and the housing includes an upper seal ring and a lower seal ring coupled together with the seal positioned therebetween for relative movement in a manner opening and closing the seal in a controlled manner;
a functional apparatus;
the seal cap also including a manifold connection including a nipple arrangement attached to the functional apparatus; and
a retractor coupled to the seal cap, the retractor including an upper retractor ring and a lower retractor ring with a retractor body extending between the upper retractor ring and the lower retractor ring, the upper retractor ring is a hollow ring connected to the nipple arrangement by a tubing member providing for fluid communication between the nipple arrangement and the upper retractor ring.

10. The laparoscopic seal asssembly according to claim 9, wherein the functional apparatus is an insufflation passageway.

11. The laparoscopic seal assembly according to claim 10, wherein the seal is an iris seal.

12. The laparoscopic seal assembly according to claim 10, wherein the insufflation passageway includes an input port located on an external side of the seal cap, and external tubing links the input port to a gas source.

13. The laparoscopic seal assembly according to claim 12, wherein the insufflation passageway further includes a lumen formed with the seal cap and the retractor.

14. The laparoscopic seal assembly according to claim 13, wherein the lumen is integrally formed within the wall of the retractor.

15. The laparoscopic seal assembly according to claim 13, wherein the lumen includes an exit port oriented to supply gas to an abdominal cavity in a manner creating a circular pattern following a natural shape of the seal cap.

16. The laparoscopic seal assembly according to claim 9, wherein the retractor further includes a lumen integrally formed in the wall of the retractor providing for fluid communication with the upper retractor ring.

17. The laparoscopic seal assembly according to claim 16, wherein the lumen includes an exit port oriented to supply gas to an abdominal cavity in a manner creating a circular pattern following a natural shape of the seal cap.

\* \* \* \* \*